United States Patent [19]

Swarbrick

[11] Patent Number: 4,731,359

[45] Date of Patent: * Mar. 15, 1988

[54] PROLONGED ACTION DRUG FORMULATION

[75] Inventor: James Swarbrick, Chapel Hill, N.C.

[73] Assignee: University of Southern California, Los Angeles, Calif.

[*] Notice: The portion of the term of this patent subsequent to Jul. 24, 2001 has been disclaimed.

[21] Appl. No.: 577,422

[22] Filed: Feb. 6, 1984

Related U.S. Application Data

[63] Continuation of Ser. No. 343,663, Jan. 28, 1982, Pat. No. 4,461,770, which is a continuation-in-part of Ser. No. 142,279, Apr. 22, 1980.

[51] Int. Cl.$^4$ .................. A61K 31/10; A61K 31/44; A61K 31/54; A61K 31/135; A61K 31/165; A61K 31/56

[52] U.S. Cl. .................. 514/169; 514/177; 514/223; 514/357; 514/618; 514/655; 514/708

[58] Field of Search ............... 424/324, 337; 514/169, 514/177, 223, 357, 618, 655, 708

[56] References Cited

PUBLICATIONS

Sinkula, "Sustained & Controlled Release Drug Del. Systems", vol. 6, Drugs & Pharm. Sciences Chapt. 6, pp. 411–548 (1978).

Primary Examiner—Stanley J. Friedman
Attorney, Agent, or Firm—Nilsson, Robbins, Dalgarn, Berliner, Carson & Wurst

[57] ABSTRACT

The time during which a drug is pharmacologically active is prolonged by coating the drug with at least one chemical derivative of the drug having minor relative pharmacological activity.

8 Claims, No Drawings

PROLONGED ACTION DRUG FORMULATION

CROSS REFERENCE TO RELATED APPLICATIONS

This application is a continuation of my application Ser. No. 06/343,663 filed Jan. 28, 1982, now U.S. Pat. No. 4,461,770 which, in turn, is a continuation-in-part of my application Ser. No. 142,279, filed Apr. 22, 1980.

FIELD OF THE INVENTION

The field of art to which the invention pertains includes the field of sustained and controlled release drug delivery systems and formulations.

BACKGROUND AND SUMMARY OF THE INVENTION

Medical science has long recognized the desirability of prolonging the time during which a drug is pharmacologically active. A significant advantage is to decrease the frequency with which the patient has to take the drug or be given the drug. This is particularly important when patient compliance problems are encountered such as with psychiatric patients or with the senile. Extending the pharmacological activity of the drug can have significant therapeutic benefits, for example, by permitting a patient to sleep undisturbed throughout the night. Perhaps most significantly, the patient is exposed to less total active drug during any given period of time, minimizing or eliminating local and systemic side effects. Prolonged action drug formulations have utility in veterinary medicine, particularly in the treatment of free-ranging animals.

A variety of methods have been devised in an attempt to increase drug release time, including oral, parenteral and topical application techniques. For example, drugs have been encapsulated in polymer or in slowly-dissolving coating material, or have been dispersed in an insoluble or slowly-dissolving matrix. Prolonged activity formulations designed for subcutaneous and intramuscular injection have been prepared by using polymers to complex or absorb the drug molecules in solution. Other techniques include suspension of polymer particles into which the drug is dispersed, suspension of microcapsules of the drug, use of solutions or suspensions of the drug in oil, or emulsions with oil, and implanting various slow release devices or pellets. These and other methods for providing prolonged activity are described in "Sustained and Controlled Release Drug Delivery Systems" by J. R. Robinson, Marcel Dekker, Inc., New York, 1978 (Volume 6 of "Drugs and the Pharmaceutical Sciences" Series, edited by J. Swarbrick).

Most pertinent to the present development are the methods described by Anthony A. Sinkula in Chapter 6 of the foregoing text relating to the chemical approach to sustained drug delivery; that Chapter 6 is incorporated herein by reference. Such methods are based upon localization of the drug in a biological depot or site within the organism with slow release to provide the active form of the drug over an extended length of time. The author describes preparation of chemical derivatives of a wide variety of drugs to increase the sustained release property of the drug molecule. In many cases, the parent molecule is regenerated in vivo by a hydrolytic mechanism. While the chemical approach would seem to offer hope for a wide variety of custom tailored prolonged action drugs, when the derivative is formulated so as to provide a significant level of drug delivery, there are a number of drawbacks pointed out by Sinkula. For example, the resulting changes in the physiochemical properties of the modified drug may well produce pharmacological and biochemical changes different from those found in the parent drug molecule. The predictability of these changes is difficult to assess, and frequently it is not possible to alter only one property of the drug. It will be appreciated that the foregoing problems arise as a result of attempting to provide a modified drug at a concentration level having substantial pharmacological activity.

The present invention provides a prolonged action drug formulation in which chemical derivatives of the desired drug are utilized, for example, as a matrix or coating within which the desired drug is located. However, in the present invention as compared to the prior use of drug derivatives, the concentration of the drug derivatives are such as to provide only minor pharmacological activity. Rather than simply relying upon regeneration of the drug by decomposition of a derivative, according to the present invention the derivatives retain their identity for an extended period of time in combination with desired quantities of the drug itself, serving by such combination to impede the release of the drug. Succinctly, the desired drug is dispersed in at least one suitable chemical derivative which has a reduced aqueous solubility and reduced dissolution rate.

It will be appreciated that there are several advantages to the present invention. In particular, since the pharmacological activity of the modified drug is minor relative to the activity of the drug with which it is in combination, there is little likelihood of pharmacological and biochemical changes in the derivative; there is thus a cost savings through reduced toxicity testing and dosage development time. The relationship between drug release and concentration in the combination can be readily determined and customized for any particular application by simple changes in concentration and/or the manner by which the drug and derivative are placed in combination. For example, it may be desirable to include free drug and combined drug-derivative particles in a particular formulation. In constrast to some prior art vehicles which are not biodegradable, the derivatives will eventually break down and be removed undergoing a reaction such as hydrolysis to reform the original drug.

More particularly, the prolonged action drug formulation of the present invention comprises a pharmacologically effective amount of a drug in solid form dispersed in or coated by at least one solid chemical derivative of the drug which has minor pharmacological activity relative to the drug, in a concentration which is sufficient to substantially prolong the time during which the drug is released and is pharmacologically active. The combination is preferably a substantially intimate and uniform mixture, for example obtained by physical admixture followed by compaction and comminution, or by coprecipitation from a common solution, or the drug and derivative can be melted together to form a fused solid; in a preferred procedure, the derivative or derivatives are coated onto, or otherwise encapsulate, particles of the drug. In this regard, one or more derivatives can be formed at the surface of the drug particles by chemical reactions as hereinafter described. The combination has particular usefulness when administered subcutaneously or intramuscularly.

The aqueous solubility (in pH 7 phosphate buffered solution) of the derivative should be less than 0.20 mg./ml., preferably less than 0.01 mg./ml. Depending upon the particular derivative and parent drug, the drug will generally constitute about 25–95 weight percent of the combination.

The prior art has used a variety of terms to characterize long-acting formulations. While one could draw distinctions between phrases such as "sustained action", "controlled release", "delayed release" and the like, as a practical matter, these terms can be used somewhat interchangeably. In this specification, the term "prolonged action" will be used to indicate all long-acting formulations, that is, formulations that have pharmacokinetic characteristics such that the formulation provides an extended length of release time than is normally found for the released drug itself.

DETAILED DESCRIPTION

It will be appreciated that the underlying concept of the present invention has applicability to a wide variety of drugs. In particular, one could utilize as the chemical derivative component an acylated derivative of the following drugs that are amenable to chemcial modification: steroids, neuroleptics, antileprotics, antimalarials, adrenergics, and antituberculars.

The present invention is exemplified with reference to the antileprotic drug diaminodiphenyl sulfone, commonly known as dapsone. This is the drug of choice in the treatment of leprosy, having strong pharmacological activity against the bacillus *Mycobacterium leprae.* Typical dosage is 50–100 milligrams per day for a period of five years or longer. Because of the chronic nature of this disease, a variety of derivative repository drugs have been proposed as substitutes for dapsone. These are described by Sinkula, supra, with optimum depot activity obtained with the diacetyl derivative of dapsone, 4', 4'''-sulfonylbisacetanilide, commonly known as acedapsone. Acedapsone is reported by Sinkula as having an aqueous solubility (pH 7 phosphate buffered solution) of 0.003 mg./ml.

When used as a "prodrug", i.e., a compound which is biotransformed into its pharmacologically active form, sufficient amount of the derivative must be used to provide the required dosage amount of the parent drug. In accordance with the present invention, when acetylated derivatives are combining with dapsone, the derivatives serve not as a source of the dapsone but physically as a matrix or coating to control the release of the dapsone with which it is present in combination. In such context, the required amount of the diacetyl dapsone derivative (acedapsone) is much lower than when it is used as a prodrug. At the concentration used in combination with dapsone, the acedapsone and monoacetyl dapsone have minor pharmacological activity relative to the dapsone component.

Other suitable parent drug-derivative combinations can be provided. For example: the steroid drug testosterone can be coated or otherwise combined with the derivative testosterone acetate; the neuroleptic drug fluphenazine can be coated with the derivative fluphenazine decanoate; the steroid drug hydrocortisone can be similarly coated with the derivative hydrocortisone propionate; the antimalarial drug cycloguanil can be coated with the lauroyl derivative of cycloguanil; the adrenergic drug dopamine can be coated with the decanoyl derivative of dopamine; and the antitubercular drug isoniazid can be combined with the lauroyl derivative of isoniazid.

Further examples can be constructed by considering the aqueous solubilities of various drug derivatives. In general, derivatives that are more soluble than 0.20 mg./ml. show little depot activity and therefore would be of little interest for the present combinations. Compounds of solubility below 0.20 mg./ml., preferably 0.01 mg./ml. or lower, are suitable candidates. Experimentally, one could determine the pharmacological activity of the derivative candidate and of the drug and combinations thereof to generate a simple concentration relationship so that a particular formulation can be customized.

The components may be intimately and uniformly dispersed which can be accomplished by compaction of a simple admixture and comminution. As an alternative to physical admixture, one can obtain a substantially intimate and uniform combination by coprecipitation of the drug with the derivative. For example, one can dissolve the drug and the derivative in a suitable solvent. The coprecipitate is prepared by either removing the solvent in vacuo or adding a liquid miscible with the solvent but in which both drug and the derivative have only a low solubility.

Another method of combining the components is to melt the combination to form a fused solid upon cooling.

A preferred method is to chemically treat particles of the drug in such a manner that the surface of each particle is converted to the desired derivative(s), thereby coating each particle with the less soluble derivative(s).

Acylated derivatives have been shown to be particularly useful in this regard, and are formed through the use of acylating agents to form N-substituted amides or esters at appropriate locations on the parent drug.

The combination can be used in accordance with any procedure in which the drug or prodrug has been used. For example, it can be suspended in aqueous solution or in oil, as appropriate, and injected as a suspension. Alternatively, the material can be implanted in the form of a pellet or as a thin wafer, or injected as microcapsules. Because a substantially smaller amount of the derivative is used in the present context than as a prodrug, one can stay within reasonable bounds of injection volume, for example 2 ml or less for subcutaneous injection and 5 ml or less for intramuscular injection.

The following examples will further illustrate the invention.

EXAMPLE I

One can combine 0.5 grams of diaminodiphenyl sulfone (dapsone) with 0.5 grams of 4', 4'''-sulfonylbisacetanilide (acedapsone) by physical admixture using a mortar and pestle. The mixture is then compressed and broken down to particles of a size than can be readily injected. The resulting mixture is suspended in 3 ml of water for injection to serve as a subcutaneous or intramuscular injection. A person suffering from leprosy is given an intramuscular injection of 3 ml (containing 1 gram of the combination), the injection being repeated only once per month.

EXAMPLE II

The procedure of Example I is repeated except that the combination is obtained by coprecipitation of the dapsone and acedapsone from common solution. In this regard, one can dissolve both dapsone and acedapsone in the minimum amount of the solvent dimethylformamide. A coprecipitate is formed on the addition of an excess of water, separated by filtration and subsequently dried. The resultant combination is treated as in Example I.

EXAMPLE III

A combination is obtained by physically admixing in a mortar and pestle 0.5 grams of dapsone and 0.5 grams of acedapsone. The combination is compressed in a suitable punch and die assembly to a pellet weighing 1.0 grams each. The pellets are then implanted subcutaneously, the wound being sutured for complete enclosure of the implant. Because of the biodegradable nature of the component, no subsequent recovery of the implant is required.

Following examples refer to coated particles having prolonged drug action, prepared by reaction of the particle surface in situ. In general terms, for surface conversion, particles of an appropriate diameter were reacted with an acylating agent (which can be as a pure liquid, present in a solution with other materials, or as a vapor alone or diluted with other gases) for a period of time sufficient to cause the desired degree of reaction at the particle surface.

EXAMPLE IV

A pellet of dapsone, formed by compressing particles at a pressure of 4,000 pounds dissolved at the rate of 0.027 mg/cm$^2$/min at 37° C. under standardized conditions. A second pellet formed in the same manner was immeresed in acetic anhydride for 10 minutes, and then warmed with water. The dissolution rate of dapsone from the second pellet was found to have fallen to 0.005 mg/cm$^2$/min.

EXAMPLE V

One gram of dapsone particles lying within the range of 104 to 208 microns were dispersed in acetic anhydride liquid at 24° C. After 1 minute the suspension was filtered, the particles so collected being washed thoroughly with water and then dried. The particles were found to contain approximately 70% of dapsone, the remainder being acetylated forms of dapsone.

EXAMPLE VI

One gram of dapsone powder, with particle size lying in the range of 104 to 208 microns was added to 35 ml of acetic anhydride in tolune (1:6 parts v/v at 24° C. in a 125 ml glass stoppered flask. The suspension was stirred for 14 minutes at which time it was filtered. The particles were washed several times with 10 ml portions of toluene and then air dried. Analysis showed the particles to contain 56% w/w dapsone, 27% w/w mono-acetylated dapsone and 17% w/w acedapsone. In other experiments conducted at 10° C., the reacted particles were found to have a composition of 83% w/w dapsone, 8% mono-acetylated dapsone and 9% acedapsone after being dispersed for 10 minutes in the 1:6 acetic anhydride/toluene solution.

EXAMPLE VII

Dapsone (0.5 gm) having a particle size within the range of 104 to 208 microns was placed in a desiccator saturated with acetic anhydride vapor at 24° C. After 120 minutes, a sample was removed, analyzed and found to contain 67.9 mole % dapsone, 7.0 mole % mono-acetylated dapsone, and 25.1 mole % acedapsone. Using a standardized dissolution procedure at 37° C., 33.4% of the dapsone was found to dissolve in 48 minutes, compared to 50.1% in the same time for unreacted dapsone of the same mean particle size.

EXAMPLE VIII

Dapsone (1.0 gm) having a particle size distribution in the range of 104 to 125 microns was rotated at 25 rpm in a small wire mesh cylinder situated inside a 500 ml round bottomed flask containing acetic anhydride vapor at 24.5° C. for a period of 20 hours. At the end of the experiment, the particles were found to contain 47.6% dapsone, 10.0% mono-acetylated dapsone and 42.4% acedapsone. Using a standardized dissolution procedure at 37° C. it was found that 57.5% of the dapsone present dissolved in 128 minutes. For unreacted dapsone of a similar size, an equivalent percentage dissolved in only 24 minutes. A sample of the reacted material was also subjected to dry heat at 110° C. for four hours. It was found that the dissolution rate was essentially unchanged.

EXAMPLE IX

The reacted material of Example VIII, containing 47.6% dapsone, was injected intramuscularly into a dog at a dose level of 40 mg/kg. A second dog received a similar dose of unreacted dapsone of the same particle size. Under steady state conditions over a nine day period, it was found that the serum level of dapsone arising from the surface reacted material was 0.95±0.15 micrograms per ml, while that for the non-reacted material was 2.75±0.49 micrograms per ml. On the basis of equivalent amounts of dapsone present, the serum levels of dapsone from the surface reacted material averaged 73% of those obtained from pure dapsone particles of the same size. Thus, the reduced dissolution rates observed in vitro were found to occur in vivo in the dog i.e., the material is being released from the muscle site more slowly than an equivalent dose of the unreacted (i.e., pure) dapsone of the same particle size.

It will be appreciated that the above listing of drugs and derivatives is not intended to be comprehensive, but merely representative of the wide variety of drugs and derivatives which can be used to constitute a combination of this invention. Those skilled in the art will know or will be able to determine by routine experimentation the many other specific drugs and derivatives that are also suitable.

What is claimed is:

1. A prolonged action drug formulated for intramuscular or subcutaneous administration, comprising in combination:
    a pharmacologically effective amount of a drug in solid particulate form, said drug being selected from steroids, neuroleptics, antileprotics, antimalarials, andrenergics, and antituberculars; and
    a solid chemical derivative of said drug in the form of a coating on particles of said drug obtained by acylation at the surface of said drug particles, said derivative having an aqueous solubility of less than 0.20 mg/ml in a concentration which is sufficient to substantially prolong the time during which said drug is pharmacologically active and having at said concentration minor pharmacological activity relative to said drug, said drug constituting about 25-95 weight percent of said formulation.

2. The formulation of claim 1 in which the aqueous solubility of said derivative is less than 0.01 mg./ml.

3. The formulation of claim 1 or 2 wherein said derivative is a monoacetyl and/or diacetyl derivative of said drug.

4. A prolonged action drug formulated for intramuscular or subcutaneous administration, comprising, in combination:
   a pharmacologically effective amount of a drug in solid particulate form, said drug being selected from testosterone, fluphenazine, hydrocortisone, cycloguanil, dopamine and isoniazid; and
   a solid chemical derivative of said drug in the form of a coating on particles of said drug obtained by reaction at the surface of said drug particles, said derivative having an aqueous solubility of less than 0.20 mg/ml in a concentration which is sufficient to substantially prolong the time during which said drug is pharmacologically active and having at said concentration minor pharmacological activity relative to said drug, said drug constituting about 25–95 weight percent of said formulation.

5. In a method for the preparation of a drug in solid particulate form, said drug being selected from steroids, neuroleptics, antileprotics, antimalarials, andrenergics, and antituberculars, the improvement according to which said drug is placed in combination with a solid chemical derivative of said drug said derivative being in the form of a coating on particles of said drug obtained by acylation at the surface of said drug, said derivative having an aqueous solubility of less than 0.20 mg/ml whereby to provide a concentration sufficient to obtain a formulation in which the time during which said drug is pharmacologically active is substantially prolonged and having at said concentration minor pharmacological activity relative to said drug, said drug constituting about 25–95 weight percent of said formulation.

6. In a method for subcutaneously or intramuscularly administering pharmacologically effective amounts of a drug in solid particulate form said drug being selected from steroids, neuroleptics, antileprotics, antimalarials, andrenergics, and antituberculars, the improvement according to which said drug is placed in combination with a solid chemical derivative of said drug, said derivative being in the form of a coating on particles of said drug obtained by acylation at the surface of said drug, said derivative having an aqueous solubility of less than 0.20 mg/ml whereby to provide a concentration sufficient to obtain a formulation in which the time during which said drug is pharmacologically active is substantially prolonged and having at said concentration minor pharmacological activity relative to said drug, said drug constituting about 25–95 weight percent of said formulation.

7. The improvement of claim 5 or 6 in which the aqueous solubility of said derivative is less than 0.01 mg./ml.

8. The improvement of claim 5 or 6 in which said derivative is a monoacetyl and/or diacetyl of said drug.

* * * * *